United States Patent [19]
Bruemmer et al.

[11] Patent Number: 5,582,606
[45] Date of Patent: Dec. 10, 1996

[54] ABSORBENT ARTICLE HAVING DUAL BARRIER MEANS

[75] Inventors: Mary A. Bruemmer; Paul J. Serbiak; Daniel R. Schlinz, all of Appleton, Wis.

[73] Assignee: Kimberly-Clarke Corporation, Neenah, Wis.

[21] Appl. No.: 447,866

[22] Filed: May 23, 1995

Related U.S. Application Data

[62] Division of Ser. No. 984,390, Dec. 2, 1992.

[51] Int. Cl.⁶ .................................. A61F 13/15
[52] U.S. Cl. .................. 604/385.2; 604/373
[58] Field of Search .................... 604/358, 373, 604/385.2

[56] References Cited

U.S. PATENT DOCUMENTS

| | | | |
|---|---|---|---|
| Re. 26,151 | 1/1967 | Duncan et al. | 128/284 |
| Re. 28,483 | 7/1975 | Ralph | 128/289 |
| Re. 30,057 | 7/1979 | Schaar | 128/287 |
| Re. 33,106 | 11/1989 | Beckestrom | 604/385.2 |
| 1,419,044 | 6/1922 | Gunderson . | |
| 1,508,740 | 9/1924 | Brand . | |
| 1,971,671 | 8/1934 | Alsop | 128/284 |
| 1,977,604 | 10/1934 | Alsop | 128/284 |
| 2,004,088 | 6/1935 | Alsop | 128/284 |
| 2,026,158 | 12/1935 | Bennett | 128/290 |
| 2,052,598 | 9/1936 | Berg | 128/288 |
| 2,078,512 | 4/1937 | Simpson | 128/283 |
| 2,141,105 | 12/1938 | Eller et al. | 128/284 |
| 2,201,255 | 5/1940 | Wilson, Jr. | 128/284 |
| 2,419,867 | 4/1947 | Woodman | 2/224 |
| 2,468,445 | 4/1949 | Hurst | 128/284 |
| 2,509,674 | 5/1950 | Cohen | 128/284 |

(List continued on next page.)

FOREIGN PATENT DOCUMENTS

| | | |
|---|---|---|
| 86044/82 | 1/1983 | Australia . |
| 21332/83 | 5/1984 | Australia . |
| 45217/85 | 2/1986 | Australia . |
| 188667 | 2/1957 | Austria . |
| 1175602 | 10/1984 | Canada . |
| 1211902 | 9/1986 | Canada . |
| 1216702 | 1/1987 | Canada . |
| 1238151 | 6/1988 | Canada . |
| 1302654 | 6/1992 | Canada . |
| 0070584A1 | 1/1983 | European Pat. Off. . |
| 0091412B2 | 10/1983 | European Pat. Off. . |
| 0098512A2 | 1/1984 | European Pat. Off. . |
| 0109126B1 | 5/1984 | European Pat. Off. . |
| 0130848B1 | 1/1985 | European Pat. Off. . |
| 0134086B1 | 3/1985 | European Pat. Off. . |
| 0149999A2 | 7/1985 | European Pat. Off. . |
| 0183668A2 | 6/1986 | European Pat. Off. . |
| 0190881A2 | 8/1986 | European Pat. Off. . |
| 0203712B1 | 12/1986 | European Pat. Off. . |
| 0219326B1 | 4/1987 | European Pat. Off. . |
| 0243013B1 | 10/1987 | European Pat. Off. . |

(List continued on next page.)

OTHER PUBLICATIONS

Partial translation of EP 251,332.
Partial translation of EP 264,952.
Partial translation of EP 268,858.
Partial translation of EP 304,631.
Partial translation of EP 346,477.
Partial tranlation of EP 409,149.

*Primary Examiner*—Robert A. H. Clarke
*Attorney, Agent, or Firm*—Thomas J. Mielke

[57] ABSTRACT

Disclosed is an absorbent article, including a pair of containment flaps, which containment flaps are particularly well suited for use on an absorbent article having a relatively narrow crotch. Specifically, the containment flaps include a proximal edge and a distal edge. The proximal edge is adhered to a bodyside liner of the absorbent product with the distal edge being adhered to the bodyside liner at a point outboard of the proximal edge. Alternatively, the proximal edge and distal edge are adhered to the bodyside liner in a manner to form a C-fold in the containment flap. The C-fold may be inboard or outboard facing.

22 Claims, 7 Drawing Sheets

U.S. PATENT DOCUMENTS

| | | | |
|---|---|---|---|
| 2,538,758 | 1/1951 | Bricmont | 128/287 |
| 2,544,069 | 3/1951 | Cutler | 128/287 |
| 2,545,674 | 3/1951 | Ralph | 128/287 |
| 2,575,164 | 11/1951 | Donovan | 128/287 |
| 2,616,427 | 11/1952 | Pettit | 128/290 |
| 2,662,526 | 12/1953 | Sanford | 128/287 |
| 2,675,805 | 4/1954 | Trimble | 128/284 |
| 2,787,271 | 4/1957 | Clark | 128/290 |
| 2,827,052 | 3/1958 | Goodman et al. | 128/284 |
| 2,840,077 | 6/1958 | Morgan | 128/284 |
| 2,893,393 | 7/1959 | Pressley | 128/287 |
| 2,895,477 | 7/1959 | Bernard | 128/284 |
| 2,916,037 | 12/1959 | Hansen | 128/284 |
| 2,964,040 | 12/1960 | Ashton et al. | 128/290 |
| 2,969,065 | 1/1961 | Farnsworth | 128/284 |
| 3,000,381 | 9/1961 | Mulhole et al. | 128/284 |
| 3,180,335 | 4/1965 | Duncan et al. | 128/287 |
| 3,182,661 | 5/1965 | Ribeiro et al. | 128/286 |
| 3,349,769 | 10/1967 | Piekarski | 128/284 |
| 3,364,931 | 1/1968 | Hirsch | 128/290 |
| 3,386,442 | 6/1968 | Sabee | 128/287 |
| 3,417,751 | 12/1968 | Murdoch | 128/287 |
| 3,426,756 | 2/1969 | Romanek | 128/287 |
| 3,449,286 | 6/1969 | Szita et al. | 604/367 |
| 3,452,753 | 7/1969 | Sanford | 128/287 |
| 3,461,872 | 8/1969 | McConnell et al. | 128/287 |
| 3,481,337 | 12/1969 | Ruffo | 128/284 |
| 3,509,881 | 5/1970 | Sabee | 128/287 |
| 3,530,859 | 9/1970 | Heimowitz | 128/284 |
| 3,532,093 | 10/1970 | Lovret | 128/286 |
| 3,572,342 | 3/1971 | Lindquist et al. | 128/287 |
| 3,575,174 | 4/1971 | Mogor | 128/290 |
| 3,592,194 | 7/1971 | Duncan | 128/287 |
| 3,593,716 | 7/1971 | Vogt | 128/287 |
| 3,612,055 | 10/1971 | Mesek et al. | 128/287 |
| 3,658,063 | 4/1972 | Schaar | 128/287 |
| 3,658,064 | 4/1972 | Pociluyko | 128/287 |
| 3,665,920 | 5/1972 | Davis | 128/287 |
| 3,667,466 | 6/1972 | Ralph | 128/287 |
| 3,744,494 | 7/1973 | Marsan | 128/287 |
| 3,771,524 | 11/1973 | Ralph | 128/287 |
| 3,776,233 | 12/1973 | Schaar | 128/287 |
| 3,779,246 | 12/1973 | Mesek et al. | 128/287 |
| 3,807,402 | 4/1974 | Miller et al. | 128/287 |
| 3,825,006 | 7/1974 | Ralph | 128/287 |
| 3,848,594 | 11/1974 | Buell | 128/284 |
| 3,860,003 | 1/1975 | Buell | 604/385.2 |
| 3,881,488 | 5/1975 | Delanty et al. | 128/287 |
| 3,884,234 | 5/1975 | Taylor | 128/287 |
| 3,885,568 | 5/1975 | Schaar | 128/287 |
| 3,890,973 | 6/1975 | Davis et al. | 128/286 |
| 3,901,236 | 8/1975 | Assarsson et al. | 128/284 |
| 3,913,578 | 10/1975 | Schaar | 128/287 |
| 3,920,017 | 11/1975 | Karami | 128/287 |
| 3,929,134 | 12/1975 | Karami | 128/284 |
| 3,930,501 | 1/1976 | Schaar | 128/287 |
| 3,930,502 | 1/1976 | Tritsch | 128/287 |
| 3,943,930 | 3/1976 | Schaar | 128/287 |
| 3,952,745 | 4/1976 | Duncan | 128/287 |
| 3,965,906 | 6/1976 | Karami | 128/287 |
| 3,978,861 | 9/1976 | Schaar | 128/287 |
| 3,987,794 | 10/1976 | Schaar | 128/287 |
| 3,995,637 | 12/1976 | Schaar | 128/287 |
| 3,995,640 | 12/1976 | Schaar | 128/287 |
| 3,999,547 | 12/1976 | Hernandez | 128/284 |
| 3,999,548 | 12/1976 | Hernandez | 128/284 |
| 4,029,100 | 6/1977 | Karami | 128/284 |
| 4,040,423 | 8/1977 | Jones, Sr. | 128/287 |
| 4,041,950 | 8/1977 | Jones, Sr. | 128/287 |
| 4,044,769 | 8/1977 | Papajohn | 128/288 |
| 4,050,462 | 9/1977 | Woon et al. | 128/287 |
| 4,069,822 | 1/1978 | Buell | 128/294 |
| 4,076,663 | 2/1978 | Masuda et al. | 260/17.4 GC |
| 4,081,301 | 3/1978 | Buell | 156/164 |
| 4,090,515 | 5/1978 | Karami | 128/284 |
| 4,100,324 | 7/1978 | Anderson et al. | 428/288 |
| 4,100,922 | 7/1978 | Hernandez | 128/284 |
| 4,129,132 | 12/1978 | Butterworth et al. | 128/287 |
| 4,166,464 | 9/1979 | Korpman | 128/287 |
| 4,182,336 | 1/1980 | Black | 128/290 R |
| 4,187,342 | 2/1980 | Holst et al. | 428/283 |
| 4,200,102 | 4/1980 | Duhamel et al. | 128/286 |
| 4,210,143 | 7/1980 | De Jonckheere | 128/287 |
| 4,210,144 | 7/1980 | Sarge, III et al. | 128/287 |
| 4,226,238 | 10/1980 | Bianco | 128/287 |
| 4,227,952 | 10/1980 | Sabee | 156/164 |
| 4,232,674 | 11/1980 | Melican | 128/287 |
| 4,239,578 | 12/1980 | Gore | 156/361 |
| 4,246,900 | 1/1981 | Schroder | 128/287 |
| 4,253,461 | 3/1981 | Strickland et al. | 128/287 |
| 4,261,782 | 4/1981 | Teed | 156/361 |
| 4,285,343 | 8/1981 | McNair | 128/287 |
| 4,286,082 | 8/1981 | Tsubakimoto et al. | 526/240 |
| 4,309,236 | 1/1982 | Teed | 156/164 |
| 4,315,508 | 2/1982 | Bolick | 128/289 |
| 4,319,572 | 3/1982 | Widlund et al. | 128/284 |
| 4,323,070 | 4/1982 | Ternstrom et al. | 128/287 |
| 4,324,245 | 4/1982 | Mesek et al. | 128/287 |
| 4,325,372 | 4/1982 | Teed | 128/287 |
| 4,326,528 | 4/1982 | Ryan et al. | 128/287 |
| 4,333,466 | 6/1982 | Matthews | 128/290 R |
| 4,352,355 | 10/1982 | Mesek et al. | 128/287 |
| 4,388,075 | 6/1983 | Mesek et al. | 604/385 |
| 4,397,645 | 8/1983 | Buell | 604/380 |
| 4,413,996 | 11/1983 | Taylor | 604/382 |
| 4,425,127 | 1/1984 | Suzuki et al. | 604/366 |
| 4,425,128 | 1/1984 | Motomura | 604/381 |
| 4,425,173 | 1/1984 | Frick | 156/204 |
| 4,430,086 | 2/1984 | Repke | 604/385 |
| 4,486,192 | 12/1984 | Sigl | 604/385 |
| 4,488,927 | 12/1984 | Hooper | 156/464 |
| 4,490,148 | 12/1984 | Beckestrom | 604/385 |
| 4,496,359 | 1/1985 | Pigneul | 604/387 |
| 4,496,360 | 1/1985 | Joffe et al. | 604/397 |
| 4,498,944 | 2/1985 | Krause et al. | 156/205 |
| 4,500,316 | 2/1985 | Damico | 604/389 |
| 4,527,989 | 7/1985 | Karami | 604/385 A |
| 4,560,380 | 12/1985 | Tharel | 604/385 R |
| 4,578,071 | 3/1986 | Buell | 604/379 |
| 4,578,073 | 3/1986 | Dysart et al. | 604/397 |
| 4,579,556 | 4/1986 | McFarland | 604/385 A |
| 4,589,876 | 5/1986 | Van Tilburg | 604/385 R |
| 4,597,760 | 7/1986 | Buell | 604/397 |
| 4,597,761 | 7/1986 | Buell | 604/397 |
| 4,601,717 | 7/1986 | Blevins | 604/358 A |
| 4,623,342 | 11/1986 | Ito et al. | 604/385 A |
| 4,626,305 | 12/1986 | Suzuki et al. | 156/164 |
| 4,636,207 | 1/1987 | Buell | 604/370 |
| 4,639,949 | 2/1987 | Ales et al. | 2/400 |
| 4,642,819 | 2/1987 | Ales et al. | 2/400 |
| 4,646,362 | 3/1987 | Heran et al. | 2/400 |
| 4,657,539 | 4/1987 | Haase | 604/385 A |
| 4,661,102 | 4/1987 | Shikata et al. | 604/385 A |
| 4,662,877 | 5/1987 | Williams | 604/385 A |
| 4,681,579 | 7/1987 | Toussant et al. | 604/385 R |
| 4,687,477 | 8/1987 | Suzuki et al. | 604/385 A |
| 4,687,478 | 8/1987 | Van Tilburg | 604/387 |
| 4,692,163 | 9/1987 | Widlund et al. | 604/385 A |
| 4,695,278 | 9/1987 | Lawson | 604/385 A |
| 4,701,177 | 10/1987 | Ellis et al. | 604/385 A |
| 4,704,115 | 11/1987 | Buell | 604/385 A |
| 4,704,116 | 11/1987 | Enloe | 604/385 A |

| | | | |
|---|---|---|---|
| 4,710,187 | 12/1987 | Boland et al. | 604/385 A |
| 4,738,676 | 4/1988 | Osborn, III | 604/385 R |
| 4,738,677 | 4/1988 | Foreman | 604/385 R |
| 4,743,246 | 5/1988 | Lawson | 604/385 A |
| 4,753,646 | 6/1988 | Enloe | 604/385 R |
| 4,762,521 | 8/1988 | Roessler et al. | 604/38 SA |
| 4,775,375 | 10/1988 | Aledo | 604/378 |
| 4,795,452 | 1/1989 | Blaney et al. | 604/385.1 |
| 4,795,454 | 1/1989 | Dragoo | 604/385.2 |
| 4,808,177 | 2/1989 | DesMarais et al. | 604/385.1 |
| 4,808,178 | 2/1989 | Aziz et al. | 604/385.2 |
| 4,816,025 | 3/1989 | Foreman | 604/385.2 |
| 4,816,026 | 3/1989 | Richardson | 604/385.2 |
| 4,822,435 | 4/1989 | Igaue et al. | 156/164 |
| 4,834,740 | 5/1989 | Suzuki et al. | 604/385.2 |
| 4,846,823 | 7/1989 | Enloe | 604/385.2 |
| 4,880,420 | 11/1989 | Pomparelli | 604/385.1 |
| 4,883,480 | 11/1989 | Huffman et al. | 604/385.1 |
| 4,883,482 | 11/1989 | Gandrez et al. | 604/385.2 |
| 4,892,528 | 1/1990 | Suzuki et al. | 604/385.2 |
| 4,900,317 | 2/1990 | Buell | 604/370 |
| 4,904,251 | 2/1990 | Igaue et al. | 604/385.2 |
| 4,909,803 | 3/1990 | Aziz et al. | 604/385.2 |
| 4,917,696 | 4/1990 | De Jonckheere | 604/385.2 |
| 4,938,754 | 7/1990 | Mesek | 604/385.2 |
| 4,938,755 | 7/1990 | Foreman | 604/385.2 |
| 4,988,344 | 1/1991 | Reising et al. | 604/368 |
| 5,021,051 | 6/1991 | Hiuke | 604/385.2 |
| 5,032,120 | 7/1991 | Freeland et al. | 604/385.2 |
| 5,080,658 | 1/1992 | Igaue et al. | 604/385.2 |
| 5,085,654 | 2/1992 | Buell | 604/370 |
| 5,087,255 | 2/1992 | Sims | 604/385.1 |
| 5,114,420 | 5/1992 | Igaue et al. | 604/385.2 |
| 5,188,627 | 2/1993 | Igaue et al. | 604/385.2 |

FOREIGN PATENT DOCUMENTS

| | | | |
|---|---|---|---|
| 0263720B1 | 4/1988 | European Pat. Off. | |
| 0264238A1 | 4/1988 | European Pat. Off. | |
| 0309246A1 | 3/1989 | European Pat. Off. | |
| 0311333A2 | 4/1989 | European Pat. Off. | |
| 0324133A1 | 7/1989 | European Pat. Off. | |
| 0329160A2 | 8/1989 | European Pat. Off. | |
| 0337969 | 10/1989 | European Pat. Off. | |
| 0374640A2 | 6/1990 | European Pat. Off. | |
| 0376022A2 | 7/1990 | European Pat. Off. | |
| 0391476A2 | 10/1990 | European Pat. Off. | |
| 0446867 | 9/1991 | European Pat. Off. | |
| 1482677 | 4/1967 | France | 604/368 |
| 2425205 | 12/1979 | France . | |
| 2554325 | 5/1985 | France . | |
| 2557774 | 7/1985 | France . | |
| 2561078 | 9/1985 | France . | |
| 2573629 | 5/1986 | France . | |
| 1070779 | 12/1959 | Germany . | |
| 1435861 | 2/1969 | Germany . | |
| 2454590 | 5/1975 | Germany . | |
| 2455778 | 6/1975 | Germany . | |
| 2521621 | 12/1975 | Germany . | |
| 2629560 | 1/1977 | Germany . | |
| 2657220 | 7/1977 | Germany . | |
| 2657221 | 7/1977 | Germany . | |
| 3039940 | 6/1981 | Germany . | |
| 3130716 | 3/1982 | Germany . | |
| 3128828 | 4/1982 | Germany . | |
| 3141963 | 5/1982 | Germany . | |
| 3216170 | 12/1982 | Germany . | |
| 3319043A1 | 11/1984 | Germany . | |
| 3439775A1 | 5/1985 | Germany . | |
| 4118359 | 8/1966 | Japan . | |
| 4118031 | 8/1976 | Japan . | |
| 62-231004 | 10/1987 | Japan . | |
| 4-297256 | 10/1992 | Japan . | |
| 4-325153 | 11/1992 | Japan . | |
| 5-293134 | 11/1993 | Japan . | |
| 667483 | 3/1952 | United Kingdom . | |
| 790062 | 2/1958 | United Kingdom . | |
| 849573 | 9/1960 | United Kingdom . | |
| 1428572 | 3/1976 | United Kingdom . | |
| 1453870 | 10/1976 | United Kingdom . | |
| 1482677 | 8/1977 | United Kingdom . | |
| 1520017 | 8/1978 | United Kingdom . | |
| 1520018 | 8/1978 | United Kingdom . | |
| 1543915 | 4/1979 | United Kingdom . | |
| 2023431 | 1/1980 | United Kingdom . | |
| 2051557 | 1/1981 | United Kingdom . | |
| 2063677 | 6/1981 | United Kingdom . | |
| 2080093 | 2/1982 | United Kingdom . | |
| 2101468 | 1/1983 | United Kingdom . | |
| 2103093 | 2/1983 | United Kingdom . | |
| 2149289 | 6/1985 | United Kingdom . | |
| 2159693 | 12/1985 | United Kingdom . | |
| 2161059 | 1/1986 | United Kingdom . | |
| 2188532 | 10/1987 | United Kingdom . | |
| 2193625 | 2/1988 | United Kingdom . | |
| 88/05269 | 7/1988 | WIPO . | |
| 93/09739 | 5/1993 | WIPO . | |

ABSORBENT ARTICLE HAVING DUAL BARRIER MEANS

This is a divisional application of copending U.S. application Ser. No. 07/984,390, filed on Dec. 2, 1992 pending.

BACKGROUND OF THE INVENTION

1. Technical Field

The present invention relates to an absorbent article having dual barrier means. Specifically, the present invention relates to an absorbent article comprising leg cuffs and containment flaps.

2. Description of the Related Art

Absorbent articles such as infant diapers, training pants, adult incontinence products, and the like are well known. Such articles have achieved a wide acceptance due to their ability to absorb body exudates without leaking. In order to achieve a high degree of leakage protection, it has become increasingly common to rely on systems wherein numerous components cooperate. For example, in the case of infant diapers, urine is generally absorbed by an absorbent core comprising a matrix of wood pulp fluff and superabsorbent material. Such an absorbent core is known to be particularly well suited for absorbing and holding urine in a diaper structure. Unfortunately, it is not always possible for the absorbent core to absorb and hold urine at the rate at which it is delivered. Thus, it has become increasingly common to rely on various mechanical containment means to hold urine within the diaper until it can be absorbed and held by the absorbent core.

For example, U.S. Pat. No. 3,860,003 issued Apr. 18, 1989, to Buell describes a diaper having elasticized leg cuffs. The leg cuffs are said to assist in the containment of body exudates. Similarly, U.S. Pat. No. 4,762,521 issued Aug. 9, 1988, to Roessler et al. describes the use of waist elastics for obtaining a tighter seal about the waist of a wearer. This also contributes to the mechanical containment of body exudates.

In an attempt to improve the mechanical containment of body exudates, it is known to employ dual mechanical containment means along the longitudinal sides of a diaper. Such a system is shown in U.S. Pat. No. 4,704,116 issued Nov. 3, 1987, to Enloe. The inner flaps are said to be particularly well suited for the containment of fecal matter while the outer leg cuffs are suited for mechanical containment of urine. As can be seen from reference to U.S. Pat. No. 4,704,116, the inner containment flaps are folded inwardly with respective ends bonded to the bodyside liner to provide a pocket-like structure. Such a dual containment system has been found to be particularly well suited for the mechanical containment of body exudates.

Inner containment flaps which are folded inwardly as described above are best suited for absorbent articles having a relatively wide crotch section. Absorbent articles having a narrow crotch region provide for a better, less bulky fit between the wearer's legs. As the crotch of an absorbent article becomes more narrow, conventional containment flaps which are folded inwardly tend to practically overlap, thereby decreasing their efficiency.

It is desired to provide inner containment flaps which are particularly well suited for use in absorbent articles having relatively narrow crotch widths.

SUMMARY OF THE INVENTION

In one aspect, the present invention resides in an absorbent article having a front portion, a rear portion, and a crotch portion connecting said front and rear portions, said crotch portion having opposite longitudinal side portions. The absorbent article includes a liquid-permeable bodyside liner, an outer cover, and an absorbent core located between the bodyside liner and the outer cover. A pair of elasticized, longitudinally-extending leg cuffs are located in the crotch portion at the opposite longitudinal side portions thereof.

Further, a pair of containment flaps are provided. The containment flaps extend longitudinally from the front portion to the rear portion and have a proximal edge and a distal edge. The proximal edge is joined to the bodyside liner in the crotch portion and in the front and rear portions. The distal edge is joined to the bodyside liner in said front portion and said rear portion outboard of the point at which the proximal edge is joined to the bodyside liner. The distal edge is unjoined to said bodyside liner in at least a portion of said crotch portion and may be elasticized in at least the crotch portion.

In another embodiment, the present invention resides in an absorbent article having a front portion, a rear portion, and a crotch portion connecting said front and rear portion, said crotch portion having oppositely disposed longitudinal side portions. The absorbent article comprises a liquid-permeable bodyside liner, an outer cover, and an absorbent core located between the bodyside liner and the outer cover. A pair of elasticized, longitudinally-extending leg cuffs are located in the crotch portion at the oppositely disposed longitudinal side portions thereof. Further, a pair of containment flaps are provided. The containment flaps extend longitudinally from the front portion to the rear portion and have a proximal edge and a distal edge. The proximal edge is joined to the bodyside liner in the crotch portion and in the front and rear portions. The distal edge is joined to the bodyside liner in at least one of the front portion or the rear portion, such that the shortest distance between the point at which the proximal edge is joined to the bodyside liner and a point at which the distal edge is joined to said bodyside liner is less than the distance between the proximal edge and the distal edge when in an unattached state, thereby forming a C-fold in the containment flap. The distal edge is unjoined to said bodyside liner in at least a portion of said crotch portion and may be elasticized in at least the crotch portion.

DETAILED DESCRIPTION OF THE PREFERRED EMBODIMENT

The present invention relates to absorbent articles designed to absorb body exudates. While the preferred embodiments of the present invention will be described in terms of a disposable infant diaper adapted to be worn by infants about the lower torso, it is understood that the present invention is equally applicable to other absorbent articles such as adult incontinent briefs, training pants, feminine care products and the like.

Figure 1:
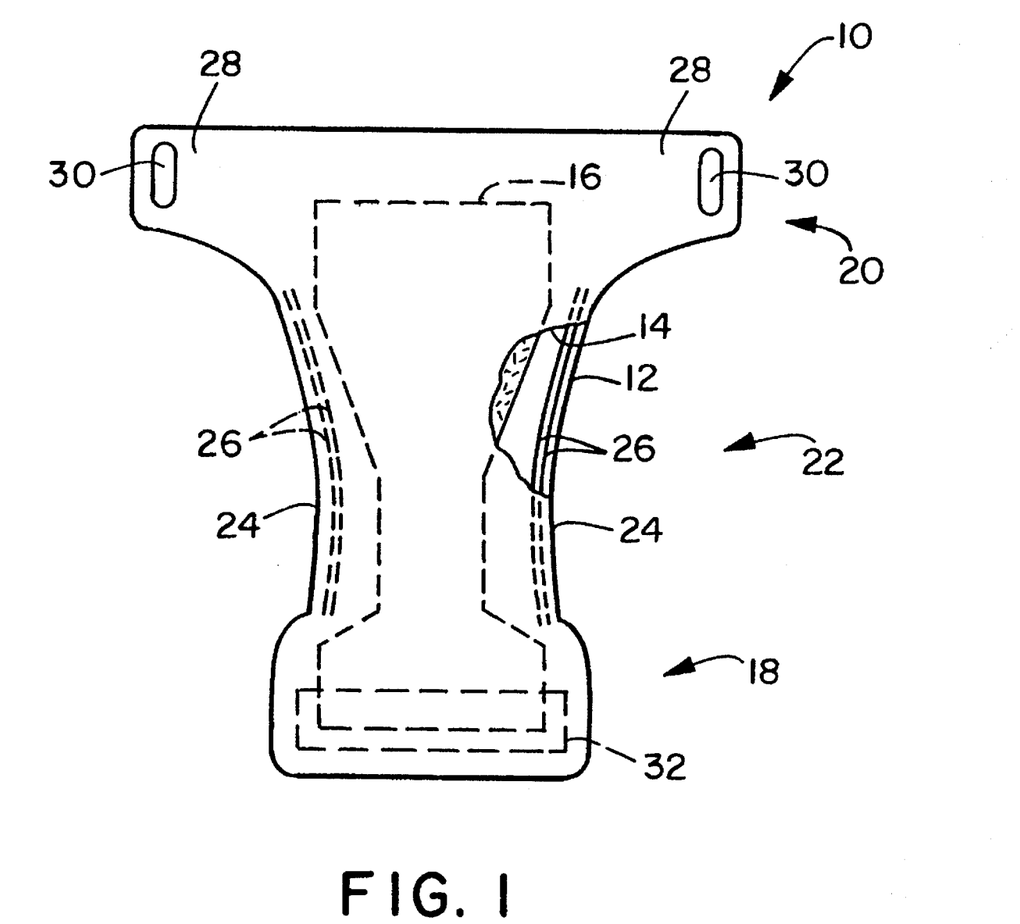
FIG. 1 illustrates a top plan view of a diaper construction suitable for use in forming the absorbent article of the present invention.

The present invention can best be understood by a reference to the drawings in which like numerals represent like elements. FIG. 1 illustrates a top plan view of a diaper suitable for use in the present invention. Fig. 1 does not illustrate a diaper having dual barrier means but is used to demonstrate the general construction of a diaper. Turning now to FIG. 1, diaper 10 comprises an outer cover 12, a bodyside liner 14, and an absorbent core 16 located between the bodyside liner 14 and the outer cover 12. Diaper 10 comprises a front portion 18, a rear portion 20, and a crotch portion 22 connecting the front portion 18 and the rear portion 20. As used herein, reference to a front portion refers to that part of the diaper which is generally located on the front of an infant when in use. Reference to the rear portion refers to the portion of the garment generally located at the rear of the infant when in use, and reference to the crotch portion refers to that portion which is generally located between the legs of an infant when in use.

The crotch portion 22 has opposite longitudinal side portions which comprise a pair of elasticized, longitudinally-extending leg cuffs 24. The leg cuffs 24 are generally adapted to fit about the legs of a wearer in use and serve as a mechanical barrier to the lateral flow of body exudates. Leg cuffs 24 are elasticized by leg elastics 26. The diaper 10 further defines ears 28 which are adapted to encircle the waist of a user. Ears 28 comprise a first fastening means 30 adapted to fasten and maintain the diaper 10 about the waist of a user. In the embodiment illustrated in FIG. 1, first fastening means 30 comprises a mechanical fastener such as the hook means of a hook and loop fastening system. First fastening means 30 is, in the illustrated embodiment, adapted to be releasably engageable with second fastening means 32 located on an outer surface of outer cover 12 in the front portion 18. The second fastening means 32 suitably comprises a loop material adapted to releasably engage with the hook material of the first fastening means 30.

Bodyside liner 14 suitably presents a body-facing surface which is compliant, soft-feeling and non-irritating to the wearer's skin. Further, bodyside liner 14 may be less hydrophilic than the absorbent core 16, to present a relatively dry surface to the wearer, and is sufficiently porous to be liquid permeable, permitting liquid to readily penetrate through its thickness. A suitable bodyside liner may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Bodyside liner 14 is suitably employed to help isolate the wearer's skin from liquids held in absorbent core 16.

Various woven and nonwoven fabrics can be used for bodyside liner 14. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 14 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The outer cover 12 may suitably be composed of a material which is either liquid permeable or liquid,d impermeable. It is generally preferred that the outer cover 12 be formed from a material which is substantially impermeable to liquids. For example, a typical outer cover can be manufactured from a thin plastic film or other flexible liquid-impermeable material. For example, the outer cover 12 may be formed from a polyethylene film having a thickness of from about 0.012 millimeter (0.5 mil) to about 0.051 millimeter (2.0 mils). If it is desired to present the outer cover 12 with a more clothlike feeling, the outer cover 12 may comprise a polyethylene film having laminated to the outer surface thereof a nonwoven web, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover may be formed of a woven or nonwoven fibrous web layer which has been totally or partially constructed or treated to impart a desired level of liquid impermeability to selected regions that are adjacent or proximate the absorbent core 16. Still further, the outer cover 12 may optionally be composed of a micro-porous "breathable" material which permits vapors to escape from the absorbent core 16 while still preventing liquid exudates from passing through the outer cover 12.

The absorbent core 16 suitably comprises a matrix of hydrophilic fibers, such as a web of cellulosic fluff, mixed with particles of a high-absorbency material commonly known as superabsorbent material. In a particular embodiment, absorbent core 16 comprises a mixture of superabsorbent hydrogel-forming particles and wood pulp fluff. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed.

Alternatively, the absorbent core may comprise a laminate of fibrous webs and superabsorbent material or other suitable means of maintaining a superabsorbent material in a localized area.

The absorbent core 16 may have any of a number of shapes. For example, the absorbent core may be rectangular, I-shaped or T-shaped. It is generally preferred that the absorbent core be narrower in the crotch portion than the rear or front portion.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic, absorbent gelling polymers are disclosed in U.S. Pat. No. 4,076,663 issued Feb. 28, 1978, to Masuda et al. and U.S. Pat. No. 4,286,082 issued Aug. 25, 1981, to Tsubakimoto et al.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like.

As a general rule, the high-absorbency material is present in the absorbent core in an amount of from about 5 to about 100 weight percent based on total weight of the absorbent core.

The outer cover 12 and bodyside liner 14 are generally adhered to one another so as to form a pocket in which the absorbent core 16 is located. Thus, leg cuffs 24 are suitably formed by portions of the outer cover 12, and/or bodyside liner 14, which extend beyond the longitudinal sides of the absorbent core 16. Naturally, the leg cuffs 24 can also be formed from separate materials which are attached to the outer cover 12 and/or bodyside liner 14.

Leg cuffs 24 include leg elastics 26. Materials suitable for use in forming leg elastics 26 are known to those skilled in the art. Exemplary of such materials are strands or ribbons of a polymeric, elastomeric material which are adhered to the diaper at the leg cuff while in a stretched position, or which are attached to the diaper while the diaper is pleated, such that elastic constrictive forces are imparted to the leg cuff 24.

Back ears 28 are suitably defined by the outer cover 12 and/or bodyside liner 14. Fastening means for attaching the diaper about the waist of a wearer are known to those skilled in the art. In the illustrated embodiment, the fastening means comprise first fastening means 30 adapted to releasably engage second fastening means 32. First fastening means 30 suitably comprises a hook material of a hook and loop fastener, while second fastening means 32 comprises the loop portion of said hook and loop fastener. The loop portion of the hook and loop fastener is attached to an outer surface of the outer cover in the front portion of the diaper.

A wide variety of other diaper configurations, as well as training pant, incontinent garment and like configurations, are suitable for use in the present invention. Further, the diapers suitable for use in the present invention may comprise numerous other elements such as waist elastics, tape fasteners and the like. Diapers suitable for use in the present invention are described in greater detail in commonly assigned U.S. patent application Ser. No. 07/757,760 entitled "Thin Absorbent Article Having Rapid Uptake of Liquid."

Figure 2:
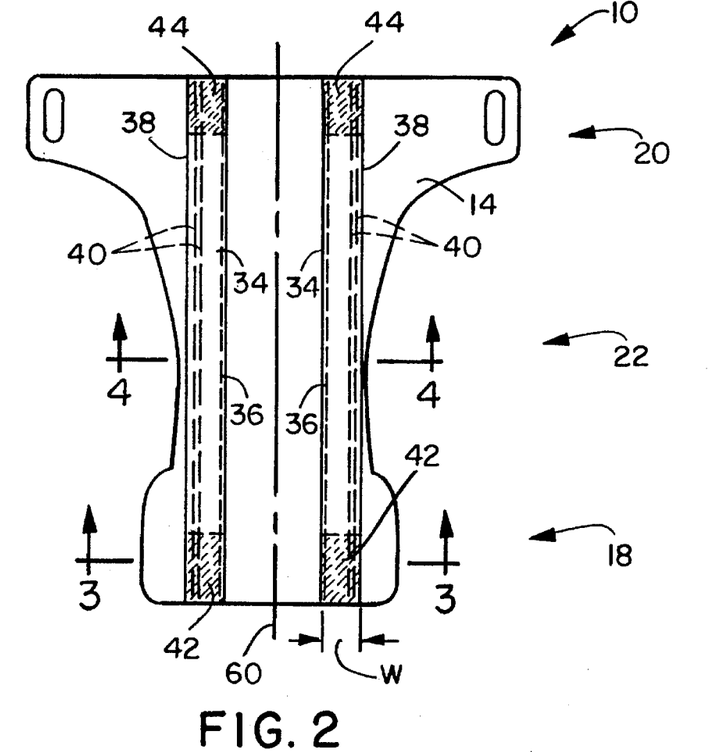
FIG. 2 illustrates a top plan view of a diaper according to the present invention.

FIG. 2 is a top plan view of a diaper according to the present invention. It is to be understood that the diaper illustrated in FIG. 2 has the same general configuration as that illustrated in FIG. 1 and described above. A number of the components of the diaper of FIG. 1 are not illustrated in FIG. 2 in order to assist in the understanding of the present invention.

With reference to FIG. 2, disposable diaper 10 comprises containment flaps 34 extending longitudinally from the front portion 18 to the rear portion 20. The containment flaps 34 have a proximal edge 36 and a distal edge 38. The proximal edge 36 of each containment flap 34 is joined to the bodyside liner 14 at least in said crotch portion. It is possible for the point of joining, between the proximal edge 36 and the bodyside liner 14, to be located inboard or outboard of leg cuff 24. In the illustrated, preferred embodiment, the point of joining between the proximal edge 36 and the bodyside liner 14 is located inboard of leg cuff 24. As used herein, the term "inboard" is intended to refer to a position located more towards the longitudinal centerline A—A of the diaper 10. Similarly, reference to the term "outboard" is intended to refer to a position located more remote from the longitudinal centerline A—A.

The distal edge 38 of each containment flap 34 is joined to the bodyside liner in the front portion 18 and the rear portion 20 outboard of the point at which the proximal edge 36 is joined to the bodyside liner. The distal edge 38 is unjoined to said bodyside liner 14 in at least a portion of said crotch portion 22. The distal edges 38 of containment flaps 34 are preferably elasticized by flap elastics 40 in at least a portion of said crotch portion 22 and, most preferably, along the entire length of said distal edge 38.

Figure 3:
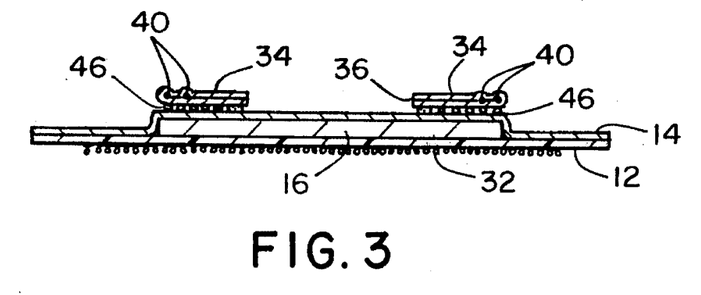
FIG. 3 is a cross-sectional view of the diaper illustrated in FIG. 2 taken along line 3—3.

In the embodiment illustrated in FIG. 2, each distal edge 38 is attached to the bodyside liner 14 in front attachment area 42 and rear attachment area 44. The attachment of the proximal edge 36 and distal edge 38 of containment flap 34 in front attachment area 42 can best be understood by reference to FIG. 3 which is a cross section of the diaper illustrated in FIG. 2 taken along line 3—3. Reference to FIG. 3 illustrates attachment means 46 present in front attachment area 42 which attaches both the proximal edge 36 and the distal edge 38 of containment flap 34 to the bodyside liner 14. In the illustrated embodiment, attachment means 46 can comprise an adhesive material such as a hot melt glue. Other attachment means, such as ultrasonic or thermal bonding, are suitable for use in the present invention.

Applicants have discovered that, by attaching the distal edge 38 of containment flap 34 outboard of the point at which the proximal edge 36 of containment flap 34 is attached to the bodyside liner, it is possible to produce a disposable diaper having a containment flap which will be relatively upright in the crotch portion 22 while still being able to function in a disposable diaper having a relatively narrow crotch. Specifically, since diaper 10 has a relatively narrow crotch, the distance between the proximal edges 36 of containment flap 34 in the crotch portion 22 is relatively small. If the distal edges 38 of containment flaps 34 were attached inboard of the proximal edge by the full width W of the containment flap 34, the distal edges 38 of the containment flaps 34 would be spaced very near one another. In such a case, much of the usefulness of the containment flaps 34 may be lost. When the distal edges 38 of the containment flaps 34 are located near one another, body exudates may be discharged on top of the containment flaps rather than in the pocket formed by the containment flaps. That is, the pocket defined by the containment flaps may have such a narrow opening that it is difficult for body exudates to pass into the area between the proximal edges of the containment flap. By attaching the distal edges 38 of containment flaps 34 outboard of the point at which the proximal edges 36 of containment flaps 34 are attached to the bodyside liner 14, the opening of the pocket defined by the containment flaps is essentially the distance between the proximal edges 36 of the containment flaps 34.

Figure 4:
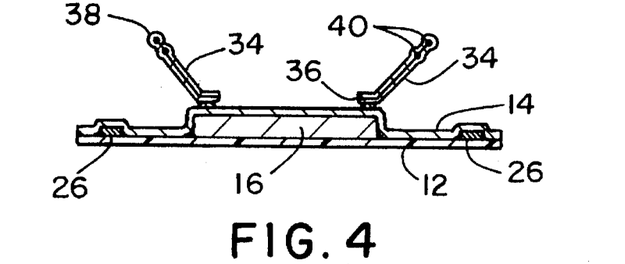
FIG. 4 is a cross-sectional view of the diaper illustrated in FIG. 2 taken along line 4—4.

FIG. 4 is a cross-sectional view of the diaper illustrated in FIG. 2 taken along line 4—4. As can be seen from reference to FIG. 4, the containment flaps 34 in the crotch portion 22 are maintained in a relatively upright position.

Figure 5:
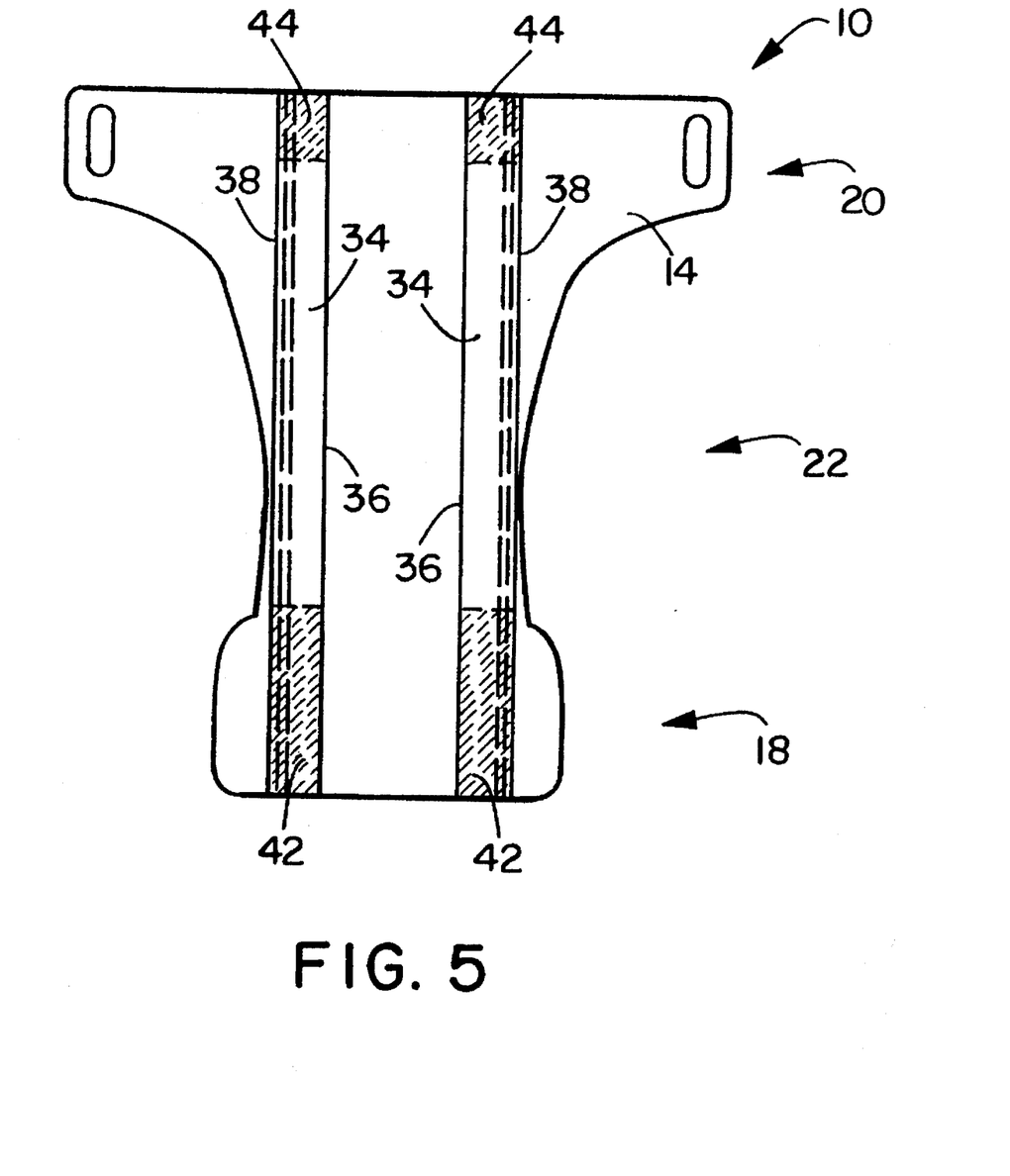
FIG. 5 is a top plan view of a diaper according to the present invention.

FIG. 5 illustrates a preferred embodiment of the present invention in which the front attachment area 42 extends along the length of containment flaps 34 a greater distance than rear attachment area 44. Specifically, it is often preferred that the front attachment area 42 extend into or almost into crotch portion 22. In this manner, it is more likely that a discharge of urine will be discharged onto the bodyside liner than onto the outboard sides of containment flaps 34. This is particularly important when the containment flaps 34 are made from a liquid-impervious material as will be discussed in greater detail below. At the same time, by having the rear attachment area 44 be relatively small compared to the front attachment area 42, the distal edges of the containment flaps 34 will still be maintained in a relatively upright position in the crotch portion 22 and rear portion 20 of the diaper 10. In this way, the containment flaps 34 will function to contain fecal matter.

Specifically, in the embodiment illustrated in FIG. 5, it is preferred that the distal edge 38 of containment flaps 34 be joined to the bodyside liner in the back portion along a first length and in the front portion along a second length wherein the second length is greater than the first length. It is preferred that the second length is at least about 25 percent greater than the first length, preferably at least about 50 percent greater than the first length, and most preferably at least about 100 percent greater than the first length. In the embodiment illustrated in FIG. 5, the distal edge 38 of containment flaps 34 is joined to the bodyside liner along its entire length in the front portion, while the distal edge 38 of containment flaps 34 is joined to the bodyside liner along less than its entire length in the back section 20.

Figure 6:
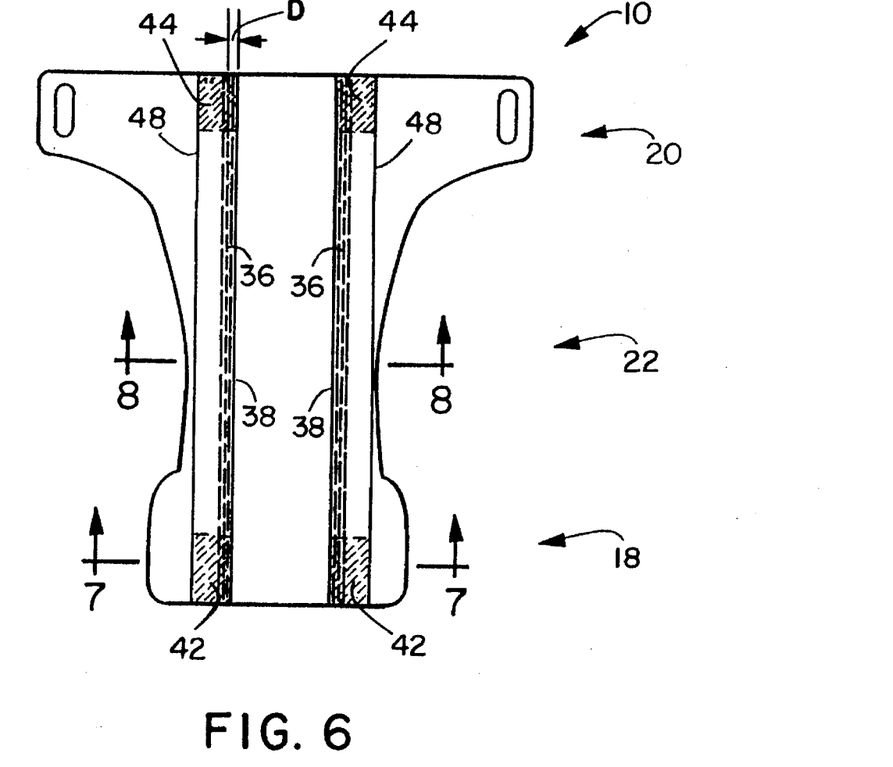
FIG. 6 is a top plan view of a diaper according to the present invention.
Figure 7:
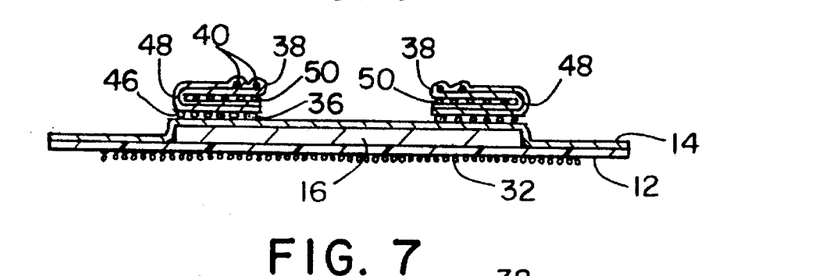
FIG. 7 is a cross-sectional view of the diaper illustrated in FIG. 6 taken along line 7—7.
Figure 8:
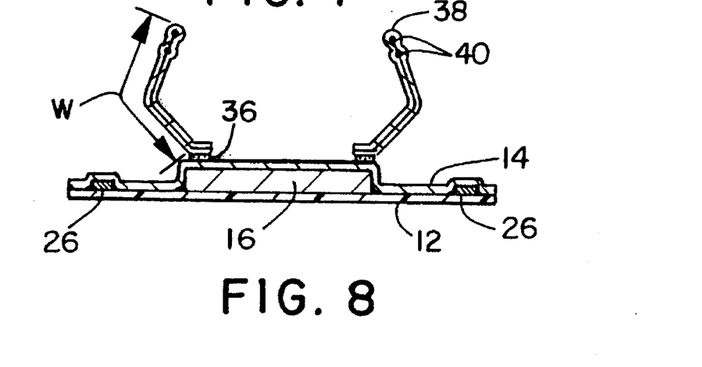
FIG. 8 is cross-sectional view of the diaper illustrated in FIG. 6 taken along line 8—8.

FIGS. 6, 7, and 8 illustrate an alternative embodiment of the present invention. As can be seen from reference to FIGS. 6–8, the containment flap 34 may be C-folded such that the distal edge 38 is joined to the bodyside liner in at least one of the front portion 18 or rear portion 20 such that the shortest distance (D), between a point at which the proximal edge 36 is joined to the bodyside liner and a point at which the distal edge 38 is joined to the bodyside liner, is less than the distance between the proximal edge 36 and the distal edge 38 when the containment flap is in a relaxed unjoined conditioned (previously referred to as the width W of containment flap 34). In this manner, a C-fold is formed in the containment flap 34. As can be seen from reference to FIG. 7, distal edge 38 is attached to the bodyside liner in front and rear attachment areas 42 and 44 such that the distal edge 38 is just slightly inboard of the proximal edge 36. The distance between the points at which the distal edge 38 is attached to the bodyside liner and the points at which the proximal edge 36 is attached to the bodyside liner in front attachment area 42 and/or rear attachment area 44 is less than the distance between the proximal edge and the distal edge when the containment flap 34 is in an unjoined extended condition. That is, the point at which the distal edge 38 is attached to the bodyside liner and the point at which proximal edge 36 is attached to the bodyside liner, in front and/or rear attachment area, is less than the width of a containment flap 34 prior to the containment flap being joined to the diaper 10. As can be seen from reference to FIG. 8, the attachment means described above produces a containment flap which is relatively upright in the crotch portion 22.

In the embodiment illustrated in FIGS. 6–8, the distal edge 38 is inboard of the proximal edge 36 in attachment areas 42 and 44. It is, of course, possible to form a C-folded containment flap such that the proximal edge 36 is inboard of the distal edge 38 in attachment areas 42 and 44.

In the embodiment illustrated in FIGS. 6–8, the containment flaps 34 define a fold line 48. The fold line 48 is formed by attaching the outboard side of containment flap 34 to bodyside liner 14 with attachment means 46. The containment flap 34 is then folded over on itself such that the inboard side of containment flap 34 is then attached to itself and/or the bodyside liner 14 with C-fold attachment means 50. Attachment means 50 is suitably an adhesive composition, ultrasonic bonding, thermal bonding or the like. The containment flap illustrated in FIG. 7 is an inboard-facing C-fold. When the containment flap 34 is C-folded, it is desirable that there be between about 20 to 100 percent, preferably between about 30 to 100 percent, and most preferably between about 40 to 100 percent overlap of the portions of the containment flap forming the C-fold in an attachment area. For example, when the containment flap is C-folded such that the proximal edge and distal edge coincide with one another in an attachment area, you have 100 percent overlap. Thus, the percent overlap refers to that portion of the width of the containment flap that is in contact with another portion of the width of the containment flap in an attachment area.

Figure 9:
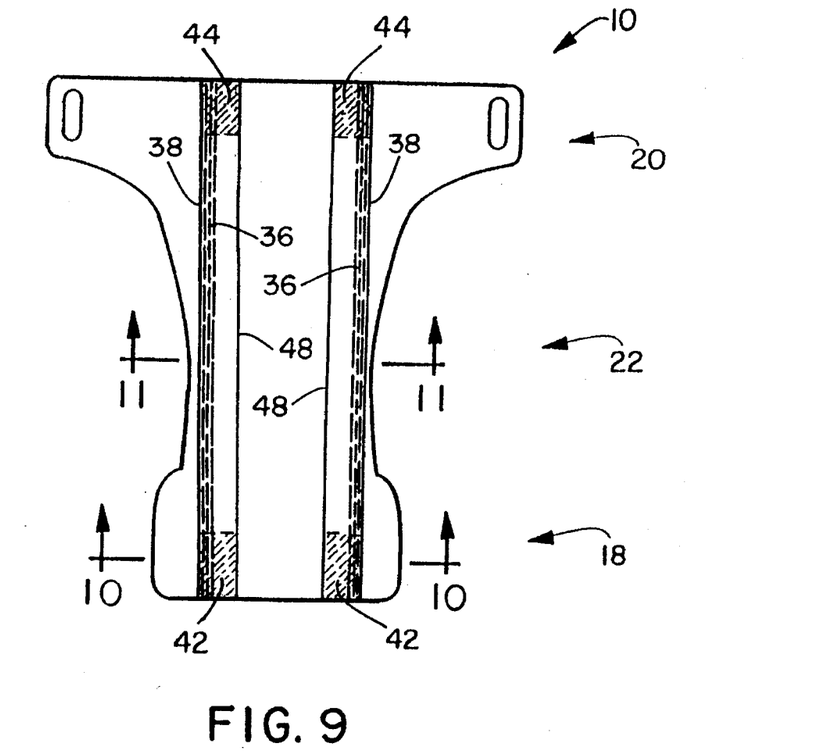
FIG. 9 is a top plan view of a diaper according to the present invention.
Figure 10:
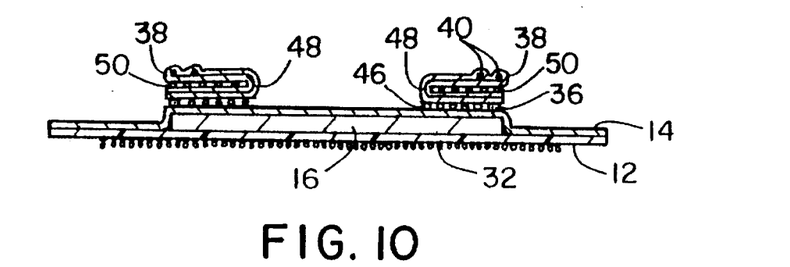
FIG. 10 is cross-sectional view of the diaper illustrated in FIG. 9 taken along line 10—10.
Figure 10A:
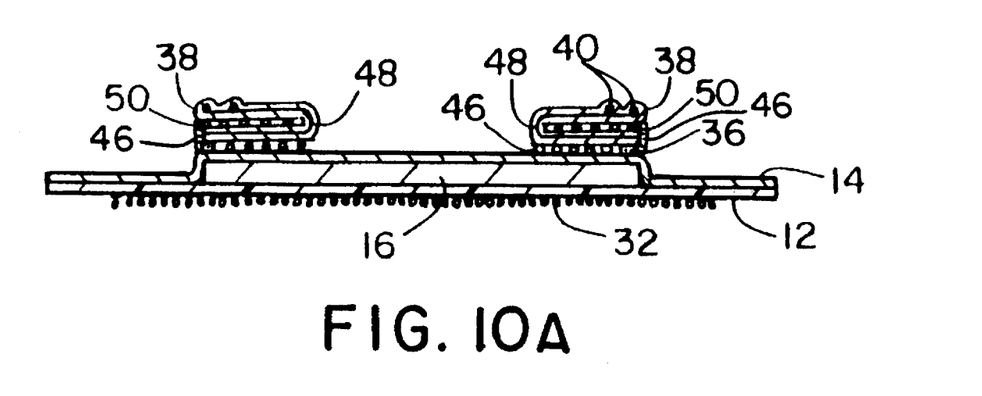
FIG. 10A is an alternative embodiment of FIG. 10.
Figure 11:
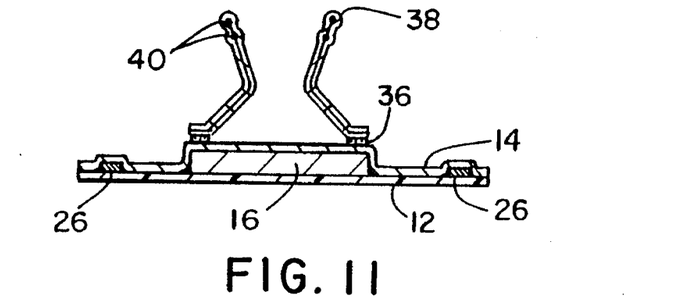
FIG. 11 is a cross-sectional view of the diaper illustrated in FIG. 9 taken along line 11—11.

Reference to FIGS. 9, 10, and 11 illustrate the embodiment wherein an outboard facing C-fold is formed. Again, the shortest distance between the point at which the proximal edge 36 is joined to the bodyside liner 14 and a point at which the distal edge 38 is joined to the bodyside liner 14 is less than the width of the containment flap when in an unattached state. As can be seen from reference to FIG. 10, fold line 48 is formed by attaching the inboard-facing side of containment flap 34 to the bodyside liner 14 with attachment means 46 and attaching the outboard-facing side of containment flap 34 to itself and/or bodyside liner 14 with C-fold attachment means 50. FIG. 10A is an alternative embodiment of FIG. 10.

It is to be understood that, while the embodiments illustrated in FIGS. 6–8 and 9–11 show the distal edge 38 being located adjacent to the bodyside liner, it is possible for the distal edge 38 to be located adjacent to the containment flap 34 such that distal edge 38 of containment flap 34 is attached to the containment flap 34. Since containment flap 34 is attached to bodyside liner 14, when distal edge 38 is attached to the containment flap 34 it is indirectly attached to bodyside liner 14. Thus, for the purposes of this application, attachment of the distal edge 38 to containment flap 34 at a point where the containment flap 34 is attached to bodyside liner 14 is considered to be attaching distal edge 38 to the bodyside liner 14.

Figure 12:
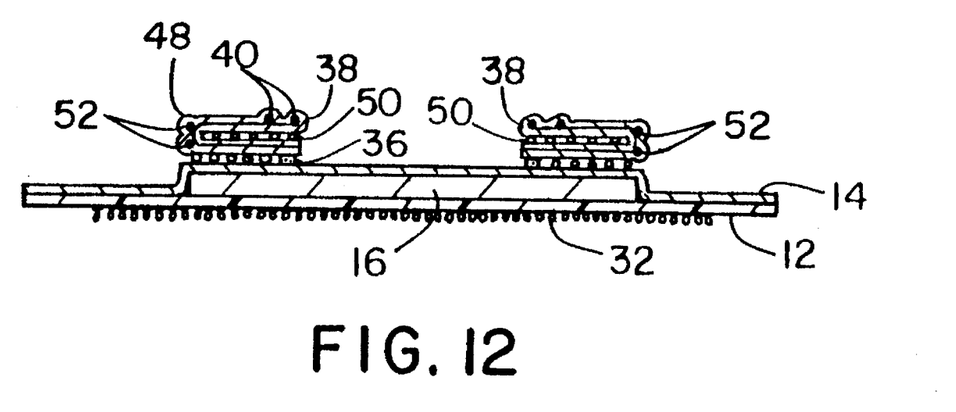
FIG. 12 is cross-sectional view through the front portion of a diaper according to the present invention showing an alternative containment flap arrangement.
Figure 13:
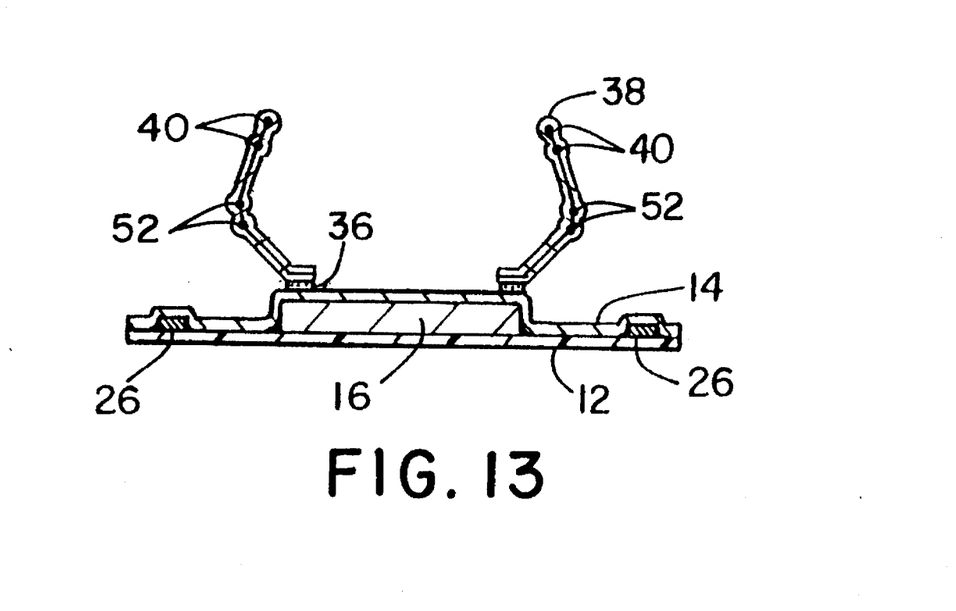
FIG. 13 is a cross-sectional view through the crotch portion of a diaper according to the present invention having the cross section illustrated in FIG. 12.

FIGS. 12 and 13 illustrate an embodiment wherein the containment flap 34 comprises a second set of elastic material. Specifically, fold line flap elastics 52 are illustrated as being positioned at the fold line 48 when containment flaps 34 are formed into a C-folded configuration. Fold line flap elastics 52 are particularly well suited for use when the containment flaps 34 have a relatively large width.

Flap elastics 40 and fold line flap elastics 52 suitably comprise one or more individual strands of elastomeric material. For example, a plurality of elastic strands may be configured in a spatially separated, generally parallel arrangement, and a suitable elastic strand can, for example, be composed of a 470 decitex Lycra® elastomer. Flap elastics 40 and fold line flap elastics 52 are suitably connected to the distal edge of the containment flap 34 in an elastically contractible condition such that the contraction of the elastic components thereof gathers and shortens the distal edge 38 of containment flap 34. As a result, the distal edge of each containment flap tends to position itself in a spaced relation away from the bodyside liner 14 toward a generally upright and approximately perpendicular configuration in especially the crotch portion of the diaper. Flap elastics 40 and fold line flap elastics 52 may suitably be formed from the same or different materials and may provide the same or different constrictive forces.

For example, flap elastics 40 may be formed from 470 decitex Lycra®, while fold line flap elastics are formed from 620 decitex Lycra®.

The containment flaps 34 may be constructed of a material which is the same or different than the material comprising bodyside liner 14. Similarly, the containment flaps may be integrally formed form the bodyside liner or may be formed separate from the bodyside liner and joined thereto. As used herein, reference to the containment flap 34 being joined to the bodyside liner 14 is intended to encompass the situation wherein the containment flap 34 is formed separately from the bodyside liner as well as the situation in which the containment flap is formed from the same material as the bodyside liner and integral therewith. The containment flap may be formed to be either liquid pervious or liquid impervious. A liquid-impervious containment flap may be formed from a polymeric film material or from a nonwoven material which has been treated so as to be substantially liquid impervious.

Methods of forming the containment flaps are known to those skilled in the art. In the illustrated embodiments, the containment flaps are formed from a double layer of material which is folded upon itself so as to encase the flap elastics 40 and/or fold line flap elastics 52 and is joined together. It is to be understood that the containment flaps could be formed from a single layer of material which has the flap elastics 40 and fold line flap elastics 52 adhered thereto.

Methods of joining the containment flaps to the bodyside liner are known to those skilled in the art. Suitable methods include heat sealing, sonic bonding, adhesive bonding, and the like. It is generally preferred that the containment flap be attached to the bodyside liner close to a lateral edge of the absorbent core in the crotch portion.

As discussed above, the containment flaps of the present invention are particularly well suited for absorbent articles having a relatively narrow crotch width. Specifically, the present invention is best suited for absorbent articles having a relatively narrow overall crotch width (width at bodyside liner and/or outer cover) and employing an absorbent core having a relatively narrow crotch width. Suitably, the absorbent article will have an overall crotch width of less than about 7 inches, desirably less than about 6 inches, beneficially less than about 5 inches, and preferably less than about 3.5 inches. The absorbent core will suitably have a crotch width of less than about 4 inches, desirably less than about 3.5 inches, beneficially less than 3 inches, and preferably less than about 2.5 inches. The containment flaps 34 of the present invention suitably have a width of from about 0.5 to about 3.5 inches, preferably of from about 1 to about 2 inches. When the width of the containment flaps 34 is greater than about 1.5 inches, it may be best suited for incorporation of fold line flap elastics 52 as described above.

Alternatively, it is preferred that the width of the crotch portion at its narrowest point be less than about 5 times, preferably less than about 4 times, and most preferably less than about 3 times the Width of the containment flap. These are the situations in Which it is most important to keep the distal edges of the containment flaps spaced as far away from one another as possible while maintaining the effectiveness of the containment flaps.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article having a front portion, a rear portion, and a crotch portion connecting said front and rear portions, said crotch portion having opposite longitudinal side portions, said article comprising:

a liquid-permeable bodyside liner;

an outer cover;

an absorbent core located between said bodyside liner and said outer cover;

a pair of elasticized, longitudinally-extending led cuffs located in said crotch portion at said opposite longitudinal side portions; and a pair of containment flaps extending longitudinally from said front portion to said rear portion and having a proximal edge and a distal edge, said proximal edge being joined to said bodyside liner in said crotch portion and in said front and rear portions, said distal edge being joined to said bodyside liner in said front portion and said rear portion outboard of the point at which the proximal edge is joined to said bodyside liner and being unjoined to said bodyside liner in at least a portion of said crotch portion wherein said containment flap is C folded in said front portion and said rear portion.

2. The absorbent article according to claim 1 wherein said C-fold is inboard facing.

3. The absorbent article according to claim 1 wherein said C-fold is outboard facing.

4. The absorbent article according to claim 1 wherein there is between about 20 to 100 percent overlap of the portions of said containment flap forming said C-fold.

5. The absorbent article according to claim 4 wherein there is between about 40 to 100 percent overlap at the portions of said containment flap forming said C-fold.

6. An absorbent article having a front portion, a rear portion, and a crotch portion connecting said front and rear-portions, said crotch portion having oppositely disposed longitudinal side portions, said absorbent article comprising:

a liquid-permeable bodyside liner;

an outer cover;

an absorbent core located between said bodyside liner and said outer cover;

a pair of elasticized, longitudinally-extending leg cuffs located in said crotch portion at said oppositely disposed longitudinal side portions; and a pair of containment flaps extending longitudinally from said front portion to said rear portion and having a proximal edge and a distal edge, said proximal edge being joined to said bodyside liner in said crotch portion inboard of said leg cuff and in said front and rear portions, said distal edge being joined to said bodyside liner in at least one of said front portion or said rear portion such that the shortest distance between a point at which said proximal edge is joined to said bodyside liner and a point at which said distal edge is joined to said bodyside liner is less than the width of the containment flap thereby forming a C-fold with portions of said containment flaps.

7. An absorbent article according to claim 6 wherein said crotch portion has an overall width of less than about 6 inches, and the absorbent core has a width in said crotch portion of less than about 4 inches.

8. An absorbent article according to claim 6 wherein said crotch portion has an overall width of less than about 5 inches, and the absorbent core has a width in said crotch portion of less than about 3 inches.

9. An absorbent article according to claim 6 wherein said crotch portion has an overall width of less than about 3.5 inches, and the absorbent core has a width in said crotch portion of less than about 2.5 inches.

10. An absorbent article according to claim 9 wherein said absorbent core is narrower in said crotch portion than in said front or rear portion.

11. An absorbent article according to claim 6 wherein said absorbent core is narrower in said crotch portion than in said front or rear portion.

12. An absorbent article according to claim 6 wherein said distal edge of said containment flap is joined to said bodyside liner in said back portion along a first length and in said front portion along a second length, wherein said second length is greater than said first length.

13. An absorbent article according to claim 12 wherein said second length is at least about 25 percent greater than said first length.

14. The absorbent article according to claim 6 wherein said distal edge is joined to said bodyside liner along its entire length in said front portion.

15. The absorbent article according to claim 14 wherein said distal edge is joined to said bodyside liner along less than its entire length in said back section.

16. An absorbent article according to claim 6 wherein there is between about 20 to 100 percent overlap of the portions of said containment flap forming said C-fold.

17. An absorbent article according to claim 16 wherein there is between about 30 to 100 percent overlap of the portions of said containment flap forming said C-fold.

18. The absorbent article according to claim 6 wherein there is between about 40 to 100 percent overlap of the portions of said containment flap forming said C-fold.

19. An absorbent article according to claim 6 wherein an inboard-facing C-fold is formed.

20. An absorbent article according to claim 6 wherein an outboard-facing C-fold is formed.

21. The absorbent article according to claim 6 wherein said distal edge is elasticized in at least a portion of said crotch portion.

22. The absorbent article according to claim 21 wherein said distal edge is elasticized along its entire length.

* * * * *